United States Patent [19]

Hoch et al.

[11] Patent Number: 6,103,223

[45] Date of Patent: Aug. 15, 2000

[54] PROCESS AND MEANS FOR PERMANENT HAIR-STYLING

[75] Inventors: Dieter Hoch, Pfungstadt; Günther Lang, Darmstadt, both of Germany

[73] Assignee: Wella Aktiengesellschaft, Darmstadt, Germany

[21] Appl. No.: 09/000,449

[22] PCT Filed: May 13, 1997

[86] PCT No.: PCT/EP97/02446

§ 371 Date: Feb. 4, 1998

§ 102(e) Date: Feb. 4, 1998

[87] PCT Pub. No.: WO97/47277

PCT Pub. Date: Dec. 18, 1997

[30] Foreign Application Priority Data

Jun. 8, 1996 [DE] Germany .......................... 196 22 999

[51] Int. Cl.$^7$ ...................................... A61K 7/06

[52] U.S. Cl. .................. 424/70.1; 424/70.2; 424/401

[58] Field of Search ................... 424/70.1, 70.12

[56] References Cited

U.S. PATENT DOCUMENTS 5,637,295  6/1997  Lang et al. ............................. 424/70.2

FOREIGN PATENT DOCUMENTS 31 19 634 A1  12/1982  Germany .

*Primary Examiner*—Thurman K. Page
*Assistant Examiner*—S. Howard
*Attorney, Agent, or Firm*—Michael J. Striker

[57] ABSTRACT

The present invention relates to a process for permanent hair-styling, characterized in that first only the hair near the scalp is fixed, with a viscous fixing agent, and then wound onto curlers, then the shafts and ends are changed into a soft wave, and the remaining length of the hair is fixed and the fixing agent is rinsed out of the hair, and to means for performing the process. A pronounced curl at the scalp and a permanent wave with a natural effect are obtained.

9 Claims, No Drawings

PROCESS AND MEANS FOR PERMANENT HAIR-STYLING

BACKGROUND OF THE INVENTION

1. Field of the Invention

The present invention relates to a process for permanent hair-styling, characterized in that first only the hair near the scalp is fixed and then the middle parts and tips of the hair shaped and then in a second step fixed, and to means for performing the process.

2. Prior Art

Permanently waving originally straight hair (called a permanent wave or perm) is known to be intended primarily to lend greater fullness and volume to a head of hair and to make the style longer-lasting.

The classic technique of performing the permanent hair-styling comprises, in a first step, opening up the disulfide bonds of the hair keratin with the aid of an agent that contains a reducing ingredient (hair-styling means); then the hair is shaped as desired; and then the disulfide bonds are linked up again, using an agent (fixing agent) that contains an oxidizing ingredient. As reducing ingredients, sulfites, thioglycolic acid, thiolactic acid, 3-mercaptoproprionic acid, mercaptocarboxylic acid and cysteine are used in particular. As the fixing agent, liquids that contain hydrogen peroxide and bromate are used in particular.

The wet hair is typically wound onto suitable shaping bodies (typically, curlers); the waving solution is then applied and after an appropriate action time is rinsed out again. The fixing agent is then applied in the form of liquid or foam to the hair, which is on curlers, and after an adequate action time is then rinsed out again; after that the hair is taken down from the curlers and re-fixed.

However, this process has a number of disadvantages. One of these disadvantages is due to the variable structure of the hair from the scalp to the tips. The middle parts and the tips, in particular, behave differently in the course of styling, as a function of aging or the effects of light and moisture as well as such previous chemical treatments as perming and coloring. As a consequence, the tips of the hair, which are especially stressed anyway, end up tightly curled, while the undamaged hair near the scalp is softly waved. This kind of overall wave pattern looks unnatural, and the resultant tangling and splitting of the tips can lead to further damage to the hair.

Moreover, as fashions in hair-styling, and the taste of the time, change, there is no longer a demand for relatively pronounced reshaping of the hair. To use the terms generally employed by customers in this respect, there is excessive and undesirable frizziness.

To attain the object of a permanent wave as stated above, however, a well-defined curl at the scalp is absolutely indispensable. If one seeks to meet this precondition with suitable provisions such as thin curlers, strong waving preparations, longer action times, etc., then as a rule the hair middle parts and the tips of the hair are necessarily waved too strongly—that is, are too frizzy—and moreover the hair structure suffers undue stress. Conversely, to achieve a desired soft or natural waving of the shank and end of the hair, the requisite tight curl at the scalp is inadequate, i.e. too weak. The teaching of published, unexamined German patent application DE-OS 3 119 634 filed by the Applicant of the present patent application seeks to solve this problem in a two-step reduction treatment by treating the entire head of hair with a weak styling means and then treating the hair near the scalp with a thickened, stronger styling means. This is intended to spare the hair and to produce a more uniform wave pattern. The disadvantage of this procedure, though, is first a more-complicated technique, and second that nevertheless there is an increased tightness of the curl at the middle parts and ends.

SUMMARY OF THE INVENTION

It has now surprisingly been discovered that all these disadvantages can be averted by proceeding in accordance with the invention, and that for the first time a uniform pattern of hair-styling, or a desired design of the waving and hence of the hair style, is possible.

The subject of the present invention is therefore a process for permanent hair-styling, which is characterized by the following process steps:

a) The washed and towel-dried hair is first wound onto curlers, preferably conventional permanent-wave curlers.

b) Next, a permanent hair-styling means known per se, based on a substance that reduces hair keratin, is applied, the effectiveness of the deformation depending on the existing hair structure.

c) The action time is determined with a test curler and amounts to from 5 to 30 minutes.

d) After the conclusion of the action time, the curlers are rinsed with water, and preferably the excess moisture is blotted up with an absorbent napkin or a hand towel.

Up to this step, the process is carried out identically to the usual waving processes known today. The novel steps in the present process, which are essential to the invention, are as follows:

e) After that, a viscous fixing agent on the basis of an oxidant is applied to the curlers, and this is followed by an action time of from 2 to 6 minutes, preferably 3 to 5 minutes.

The viscous fixing agent differs from conventional agents of this type in having such a high viscosity that while thorough fixing of the wave at the hair near the scalp is assured, at the same time premature penetration of the middle parts and tips of the hair on the curlers by the fixing agent is prevented or markedly delayed.

f) After the action time of the fixing agent on the hair near the scalp elapses, the hair is taken down and the curlers are removed.

Since at this time the middle parts and tips of the hair have not yet been sufficiently well fixed and stabilized, in this condition of the hair it is possible to transform what is as a rule an overly pronounced waving of these portions of the hair into a soft, natural curl.

The "transformation" is carried out as follows:

g) The curls, still tight and cohesive, are loosened with a preferably wide-toothed comb, the hands, or a hair brush and combed into the desired style. At the same time, the still overly tight frizziness at the tips is relaxed individually and in a specific way for a particular style and changed into a soft, natural kind of curl. A fine-toothed comb can also be used for this latter purpose.

In another embodiment, it is also possible for the "transformation" to comb the taken-down hair into the desired style using an appliance suited to styling hair at elevated temperature, in particular a round hair brush heated electrically or with heated air, or a curling iron or similar shaping body, or a round hair brush and a handheld hair dryer.

In a further embodiment of the process according to the invention, in the process step for the "transformation" the hair, instead of being combed, can be wound onto rollers (for instance with a diameter of from 15 to 30 mm, such as water-setting rollers or similar large-sized rollers) and then further treated as described below.

Since at the time of the transformation the requisite stronger curl at the hair near the scalp is already fixed and stabilized, it remains unaffected by the transformation; that is, it is preserved to its full extent.

h) Once the desired waving pattern is attained, the remaining length of the hair (middle part or shaft and tips) is likewise treated with a fixing agent on the basis of an oxidant.

For this purpose, either the viscous fixing agent can be worked into all the hair (by combing it in, for example), or a commercially available low-viscosity fixing solution (fixing rinse) can be used. In the latter case, a 2-component fixing agent is used, to save time.

i) After a further action time of from 1 to 10 minutes, preferably 3 to 5 minutes, the fixing agent is rinsed out of the hair with water.

If an additional low-viscosity fixing solution is used for the middle parts and tips, the action time can be omitted.

All the usual means and agents of this kind are suitable as hair-styling means. The styling means can be in the form of an aqueous solution or an emulsion or in thickened form on an aqueous base, in particular in the form of a cream, gel or paste.

In the permanent hair-styling means ready for use, the substances that reduce hair keratin that are contained in the permanent hair-styling means are used preferably in a quantity of from 2 to 20 weight %, and especially preferably in a quantity of from 4 to 12 weight %, and very particularly preferably in a quantity of from 6 to 10 weight %.

Examples of hair keratin reducing substances that can be used are thioglycolic acid, thiolactic acid, cysteine, cysteamine, alkyl or acyl cysteamines, or the salts of these compounds, as well as thioglycolic acid esters or sulfites, especially in the acidic pH range, including in mixture with one another.

The permanent hair-styling means ready for use preferably have a pH value of from 6 to 9, and especially preferably from 6.5 to 8.5. As alkalizing agents or as means for adjusting the pH value, ammonia or sodium hydroxide solution can be considered particularly, but also all other water-soluble, physiologically acceptable salts of organic and inorganic bases, such as ammonium hydrogen carbonate, can be considered.

The permanent hair-styling means can be made up in the form of a one-, two- or three-component preparation, and it can be in the form of either an aqueous solution or an emulsion or in thickened form on an aqueous base, in particular in the form of a cream, gel or paste.

Thus the permanent hair-styling means can be obtained for instance by mixing two components, of which the first component contains at least one alkalizing agent such as an alkali carbonate, ammonium carbonate, alkali hydrogen carbonate or ammonium hydrogen carbonate, and the substance that reduces hair keratin, and the second component contains at least one of the cosmetic additives listed below, plus water.

It is equally possible to package the permanent hair-styling means in the form of a three-component preparation, in which one component contains some of the cosmetic additives listed below, plus water; a second, water-free component contains the substance that reduces hair keratin, and the third component contains further additives, such as perfume oils, solubilizers and conditioners, in aqueous solution or in water-free form.

In all the embodiments of the permanent hair-styling means, the cosmetic additives may be contained in both the aqueous and/or nonaqueous component or components.

It is understood that the permanent hair-styling means may contain all the conventional and known additives for such means, for example thickeners, such as bentonite, fatty acids, starch, polyacrylic acid and its derivatives, cellulose derivatives, alginates, vaseline, and paraffin oils; wetting agents or emulsifiers selected from the classes of anionic, cationic, amphoteric or nonionic surfactant substances, such as fatty alcohol sulfates, fatty alcohol ether sulfates, alkyl sulfonates, alkyl benzene sulfates, quaternary ammonium salts, alkyl betaines, ethoxylated alkyl phenols, fatty acid alkanolamides or ethoxylated fatty acid esters; and also opacifiers, such as polyethylene glycol esters; alcohols, such as ethanol, propanol, isopropanol and glycerine; sugar, such as D-glucose; solubilizers, stabilizers, buffer substances, perfume oils, colorants, and hair conditioning and hair care ingredients, such as kationic polymers, lanolin derivatives, cholesterol, pantothenic acid, and betaine.

The aforementioned ingredients are used in the usual quantities for such purposes; for example, the wetting agents and emulsifiers may be contained in this means in concentrations of a total of 0.2 to 30 weight %, the alcohols in a total quantity of 0.1 to 20 weight %, the opacifiers, perfume oils and colorants in a quantity of 0.01 to 1 weight % each, the buffer substances in a total quantity of 0.1 to 10 weight %, and the sugar, solubilizers, stabilizers and hair conditioning and hair care ingredients each in a quantity of 0.1 to 5 weight %, while the thickeners and solubilizers may be contained in a total quantity of 0.5 to 20 weight %.

To increase its effectiveness, so-called swelling and penetration substances can be added to this means as well, such as diproplylene glycol monomethyl ether; 2-pyrrolidone or imidazolidin-2-one, in a quantity of 1 to 30 weight %, and to avoid making the hair frizzy, dithio compounds can be added, such as dithioglycolic acid, dithiolactic acid, the dithiols of these compounds, or the respective salts, again in a quantity of from 1 to 30 weight %.

After an adequate action time for permanently waving the hair, which depending on the nature of the hair, the pH value, and the permanent-waving effectiveness of the permanent hair-styling means, as well as on the application temperature, can be from 5 to 30 minutes (20 to 30 minutes if heat is not applied; 15 to 25 minutes with the application of heat), the hair is rinsed with water. The rinsing operation preferably lasts from 2 to 4 minutes. After that, it is advantageous to dry off the curlers with an absorbent napkin or a hand towel. The application temperature when heat is applied is in the range from 30 to 45° C.

The viscous fixing agent is characterized in that it has a viscosity such that premature penetration of the fixative into the middle parts and tips of the hair on the curlers is prevented or markedly delayed; that is, it is in thickened form on an aqueous basis, in particular in the form of cream, gel, suspension or paste, or as a viscous foam. Preferably it has a viscosity of 50 to 5000 mPa·s at 25° C., especially preferably from 100 to 3000 mPa·s at 25° C., and very particularly preferably from 100 to 1000 mPa·s at 25° C., measured for instance with a Haake rotary viscosimeter type VT 550 at a shear rate of 50 per second.

As thickeners, both polymeric thickeners such as polyacrylic acid and its derivatives, cellulose derivatives, alginates and chitin or chitosin derivatives, as well as surfactant systems (emulsions, microemulsions, suspensions and viscous liquid crystalline phases) and combinations of suitable emulsifiers selected from the classes of anionic, cationic, amphoteric or nonionic surfactant substances, such as fatty alcohol sulfates, fatty alcohol ether sulfates, alkyl sulfonates, alkyl benzene sulfates, quaternary ammonium salts, alkyl betaines, ethoxylated alkyl phenols, ethoxylated fatty alcohols, fatty acid alkanolamides or ethoxylated fatty acid esters with suitable fatty phases such as fatty alcohols, fatty acid amides, fatty acid glycerides and fatty acid glycolates, vaseline and paraffin oils and paraffin waves, as well as inorganic thickeners such as bentonites, can be considered. The thickeners are preferably contained in a total quantity of 1 to 30 weight %.

Examples of oxidants that can be used in fixing agents are potassium bromate and sodium bromate, sodium perborate, urea peroxide and hydrogen peroxide. The concentration of the oxidant varies, depending on the type of oxidant, the application time (as a rule, from 5 to 15 minutes) and the application temperature. Normally, the oxidant in the ready-to-use viscous fixing agent is in a concentration of from 1 to 15 weight %. Preferably, the viscous fixing agent contains hydrogen peroxide in a quantity of from 1 to 5 weight % or bromate in a quantity of from 5 to 15 weight %.

The agent for the oxidative post-treatment can naturally contain still other substances, such as wetting agents, conditioners such as cationic polymers, weak acids, conditioners such as cationic polymers, weak acids, buffer substances, or peroxide stabilizers.

For performing process step h), either the viscous fixing agent can be worked into the entire head of hair, or any arbitrary fixing agent previously used for such a treatment can be used.

The following examples are intended to explain the invention in further detail, but without limiting the subject to these examples.

EXAMPLES

Example 1

Undamaged hair is washed with a shampoo, towel dried, and wound onto curlers with a diameter of 8 millimeters. Next, the permanent-waving solution, with a pH of 8.2, is applied evenly to the hair on the curlers, using a bottle with an applicator nozzle.

| Permanent-waving solution | |
|---|---|
| 10.00 g | thioglycolic acid |
| 6.10 g | ammonium hydrogen carbonate |
| 7.60 g | ammonia, 25% aqueous solution |
| 1.00 g | castor oil, ethoxylated with 35 mol ethylene oxide |
| 0.20 g | cocoamphoglycinate (CTFA: sodium cocoamphoacetate) |
| 0.50 g | perfume oil |
| 74.60 g | water |
| 100.0 g | |

The hair is then covered with a plastic hood and heated for 10 minutes under the dryer at a temperature of 40° C. Next, the covering is removed and the hair on the curlers is rinsed with warm water for 2 to 3 minutes, and the excess moisture is blotted from the curlers with a terry cloth hand towel. After that, 60 g of the following viscous fixing agent is applied to the curlers with a paint brush.

| Viscous fixing agent with hydrogen peroxide | |
|---|---|
| 2.00 g | cetyl stearyl alcohol |
| 0.20 g | disodium phosphate |
| 0.15 g | orthophosphoric acid |
| 0.20 g | sodium lauryl sulfate |
| 4.00 g | hydrogen peroxide, 50 weight % |
| 0.30 g | perfume oil |
| 0.10 g | vinyl pyrrolidone and styrene copolymer (Antara$^R$ 430, GAF Corp., New York) |
| 93.05 g | water |
| 100.00 g | |

An action time of 3 minutes follows.

Once the action time has elapsed, the curlers are taken down, and the relatively pronounced waving in the shafts of the hair, which except for the hair near the scalp is not yet fixed, is transformed to the desired intensity of the reshaping with a comb. Once the desired condition is reached, a further 50 g of the above viscous fixing agent is distributed throughout the hair and worked in. Another action time of 5 minutes follows. After that, the hair is rinsed thoroughly again with warm water. This completes the actual treatment. It is followed by the usual final styling using a handheld hair dryer and a hair brush.

Example 2

Oxidatively damaged and permed hair is washed with a shampoo, towel dried, and wound onto curlers with a diameter of 8 millimeters. Next, the permanent-waving solution is applied evenly to the hair on the curlers.

Neutral permanent-waving solution comprising 2 components

| Component A | |
|---|---|
| 94.6 g | ammonium thioglycolate, 70% aqueous solution |
| 5.4 g | cysteine hydrochloride |
| 100.0 g | |
| Component B | |
| 0.8 g | ammonia, 25% aqueous solution |
| 0.5 g | ammonium hydrogen carbonate |
| 2.0 g | lauryl alcohol, ethoxylated with 4 mol ethylene oxide |
| 1.0 g | polydimethyldiallylammonium chloride |
| 1.0 g | perfume oil |
| 0.5 g | vinyl pyrrolidone and styrene copolymer |
| 0.5 g | cetyltrimethylammonium chloride |
| 93.7 g | water |
| 100.00 g | |

Component B has a pH value of 8.5. Before use, 15 g of component A and 66 g of component B are mixed with 81 g of the ready-to-use hair-styling means that has a pH of 7.5.

The hair is then treated for 10 minutes with an infrared heating hood at the "permanent wave" temperature setting. Next, the hair on the curlers is rinsed for 3 minutes with warm water, and the excess moisture is blotted from the curlers with a terry cloth hand towel. After that, 60 g of the viscous fixing agent below is applied to the curlers with a paint brush.

| Viscous fixing agent with bromate | |
|---|---|
| 11.0 g | sodium bromate |
| 6.0 g | cetyl stearyl alcohol |
| 2.0 g | vaseline |
| 2.0 g | cetyl stearyl alcohol ethyoxylated with 25 mol of ethylene oxide (CTFA: Ceteareth 25) |
| 1.0 g | cetyltrimethylammonium chloride |
| 1.0 g | poly(dimethyldiallylammonium chloride) |
| 0.3 g | perfume oil |
| 0.5 g | sodium phosphate |
| 1.0 g | disodium phosphate |
| 0.1 g | vinyl pyrrolidone and styrene copolymer (Antara$^R$ 430, GAF Corp., New York) |
| 75.1 g | water |
| 100.0 g | |

An action time of 3 minutes follows.

Once the action time has elapsed, the curlers are taken down, and the relatively pronounced waving in the shafts of the hair, which except for the hair near the scalp is not yet fixed, is transformed to the desired intensity of the reshaping with a comb. Once the desired condition is reached, a further 50 g of the above viscous fixing agent is distributed throughout the hair and worked in. Another action time of 5 minutes follows. After that, the hair is rinsed thoroughly again with warm water. This completes the actual treatment. The hair thus shaped is air-dried under the infrared heating hood without any additional mechanical aids.

What is claimed is:

1. A method of permanent shaping of hair on a scalp, in which only a first portion of the hair near the scalp is fixed in a first stage and then in a second stage a second portion of the hair consisting of the middle parts and tips of the hair is fixed as well as said first portion of the hair near the scalp; said method comprising the steps of:

a) winding the hair onto curlers;

b) providing a permanent hair-styling composition comprising a hair keratin-reducing substance for reducing hair keratin and a viscous fixing composition having a viscosity from 50 to 5000 mPa-sec at 25° C. and including an oxidizing agent, wherein said permanent hair-styling composition has a pH of 6 to 9 and wherein said permanent hair-stylina composition consists essentially of from 2 to 20% by weiaht of at least one reducing ingredient acting as said hair keratin-reducing substance and selected from the group consisting of thioglycolic acid, salts of thioglycolic acid, esters of thioglycolic acid, thiolactic acid, salts of thiolactic acid, cysteine, salts of cysteine, cysteamine, salts of cysteamine, alkyl cysteamines, acyl cysteamines and thioglycolic acid sulfites; an alkalizing agent; water; and at least one cosmetic additive selected from the group consisting of wetting agents, emulsifiers, alcohols, opacifiers, perfume oils, colorants, buffer substances, sugars, solubilizers, stabilizers, swelling and penetrating substances, hair conditioning ingredients, hair care ingredients and thickeners;

wherein said permanent hair-styling composition contains no diquaternary polysiloxanes, but contains from 0.2 to 30 percent by weight of a total amount of said wetting agents and said emulsifiers when at least one of said wetting aaents and emulsifiers is present therein; from 0.1 to 20 percent by weight of a total amount of said alcohols when at least one of said alcohols is present therein; from 0.01 to 1 percent by weight of a total amount of said opacifiers, said perfume oils and said colorants when at least one of said opacifiers, said perfume oils and said colorants is present therein; from 0.1 to 10 percent by weight of a total amount of said buffer substances when at least one of said buffer substances is present therein; from 0.1 to 5 percent by weight of a total amount of said sugars, said solubilizers, said stabilizers, said hair conditioning ingredients and said hair care ingredients when at least one of said sugars, said solubilizers, said stabilizers, said hair conditioning ingredients and said hair care ingredients is present therein; from 0.5 to 20 percent by weight of a total amount of said thickeners and said solubilizers when at least one of said thickeners and said solubilizers is present therein; and from 1 to 30 percent by weight of said swelling and penetrating substances when at least one of said swelling and penetrating substances is present therein; and wherein said viscous fixing composition contains from 1 to 15 percent by weight of at least one oxidizing ingredient acting as said oxidizing agent and selected from the group consisting of potassium bromate, sodium bromate, sodium perborate, urea peroxide and hydrogen peroxide and from 1 to 30 percent by weight of at least one thickener selected from the group consisting of polymeric thickeners, surfactant systems, combinations of emulsifiers and inorganic thickeners;

c) applying the permanent hair-styling composition to the hair wound on the curlers in step a);

d) allowing the permanent hair-styling composition applied to the hair in step c) to act on the hair for an acting time of from 5 to 30 minutes;

e) after the allowing of step d), rinsing the permanent hair-styling composition from the hair wound on the curlers with water;

f) after the rinsing of step e), applying the viscous fixing composition to the hair and allowing said viscous fixing composition to act on the hair only for an acting time of from 2 to 6 minutes, said viscous fixing composition having a viscosity great enough and said acting time being short enough, so that said first portion of said hair comparatively close to the scalp is thoroughly fixed while penetration of said second portion of said hair comparatively far from the scalp by said viscous fixing composition is prevented;

g) removing the hair from the curlers, after the applying of the viscous fixing composition to the hair and the allowing of the viscous fixing composition to act on the hair in step f);

h) after the removing of step g), combing the hair into a desired style with a comb, hands of a stylist or a hair brush and simultaneously relaxing tight frizziness at the tips of the hair to form a soft natural curl, or combing the hair into the desired style with an appliance suited to styling the hair while heating the hair, or winding the hair onto rollers having a diameter of from 15 to 30 mm, in order to transform excessive deformation of the hair at the tips into a soft wave;

i) after the combing of the hair or the winding of the hair onto the rollers in step h), treating the hair with a hair fixing preparation containing an oxidant; and j) after the treating of the hair with the hair fixing preparation in step i), allowing the hair fixing preparation to act on the hair for from 1 to 10 minutes and after that, rinsing the hair fixing preparation from the hair with water;

whereby a uniform hair styling from the first portion of the hair near the scalp to the tips results.

2. The method as defined in claim 1, wherein said appliance is an electrically heated round brush, an air-heated round hair brush, a curling iron or a round hair brush operating together with a hand-held hair dryer.

3. The method as defined in claim 1, further comprising heating the hair at a temperature of from 30 to 45° C. during the applying of the permanent hair-styling composition to the hair.

4. The method as defined in claim 3, wherein said heating of the hair is performed with an infrared radiating appliance.

5. The method as defined in claim 1, wherein said acting time for said permanent hair-styling composition applied to the hair is from 20 to 25 minutes for normal hair that was not previously treated oxidatively and from 15 to 20 minutes for oxidatively treated hair.

6. The method as defined in claim 1, wherein said acting time for said permanent hair-styling composition applied to the hair is determined from a test with a single test curler.

7. The method as defined in claim 1, wherein the hair is blotted with an absorbent napkin or hand towel after the rinsing of the permanent hair-styling composition from the hair wound on the curlers.

8. The method as defined in claim 1, wherein said hair fixing preparation consists of said viscous fixing composition.

9. The method as defined in claim 8, wherein said viscous fixing composition is allowed to act on the hair for from 3 to 5 minutes and said hair fixing preparation is allowed to act on the hair for from 3 to 5 minutes.

* * * * *